United States Patent
MacCulloch

[19]

[11] Patent Number: 6,139,321
[45] Date of Patent: Oct. 31, 2000

[54] DEVICE FOR DISPENSING ARTIFICIAL TEETH

[76] Inventor: William Thomson MacCulloch, 45 Springmount Road, Glanmire, County Cork, Ireland

[21] Appl. No.: 09/308,982

[22] PCT Filed: Dec. 11, 1997

[86] PCT No.: PCT/IE97/00083

§ 371 Date: May 28, 1999

§ 102(e) Date: May 28, 1999

[87] PCT Pub. No.: WO98/26728

PCT Pub. Date: Jun. 25, 1998

[30] Foreign Application Priority Data

Dec. 16, 1996 [IE] Ireland .................................. S960890

[51] Int. Cl.[7] .............................................. A61C 13/10
[52] U.S. Cl. ............................................ 433/196; 433/171
[58] Field of Search .................... 433/26, 167, 171, 433/196, 191, 199.1

[56] References Cited

U.S. PATENT DOCUMENTS

| | | |
|---|---|---|
| 1,550,905 | 8/1925 | Kesling .................................. 433/196 |
| 1,692,928 | 11/1928 | Clapp et al. ............................. 433/196 |
| 1,696,422 | 12/1928 | Thayler .................................. 433/196 |
| 2,641,835 | 6/1953 | Greenmun ............................. 433/199.1 |
| 4,705,476 | 11/1987 | Blair ........................................ 433/171 |

FOREIGN PATENT DOCUMENTS

| | | |
|---|---|---|
| 0 130 598 | 1/1985 | European Pat. Off. . |
| 39 10 393 | 10/1990 | Germany . |
| 1711862 | 2/1992 | U.S.S.R. ................................ 433/167 |

*Primary Examiner*—Ralph A. Lewis
*Attorney, Agent, or Firm*—Young & Thompson

[57] ABSTRACT

A device for dispensing artificial teeth comprises a tooth support ribbon (2) which is made from a flexible material and is shaped to form an arch which substantially corresponds in shape to an upper or lower natural dental arch. A set (10) of artificial teeth (11, 12) is removably mounted on the support ribbon 92) by a slot (13) in each tooth which engages with a key (16) in the ribbon (2). The teeth are arranged on the ribbon (2) in an order which simulates natural dentition. The radius of the arch may be adjusted by an extensible cross-member (3) connected at each end to the ribbon (2) and extending across the arch.

10 Claims, 3 Drawing Sheets

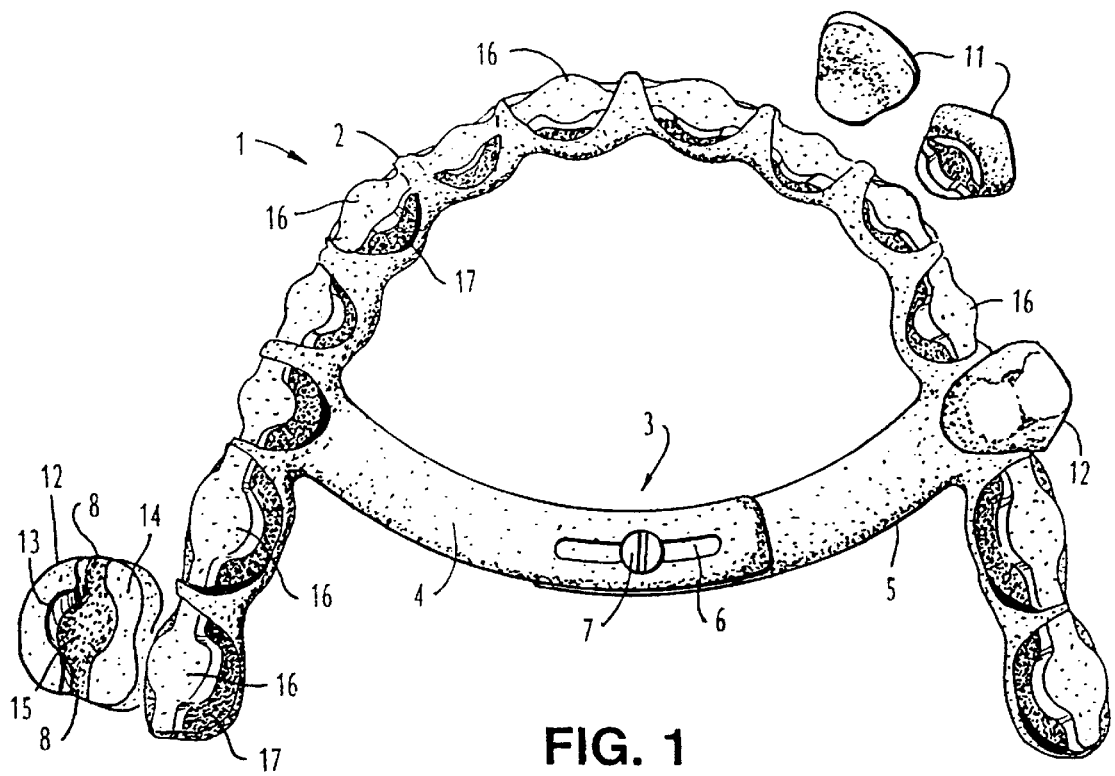
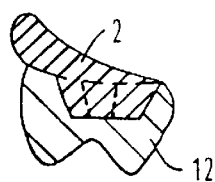
FIG. 4
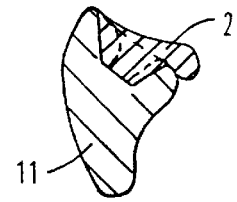
FIG. 3
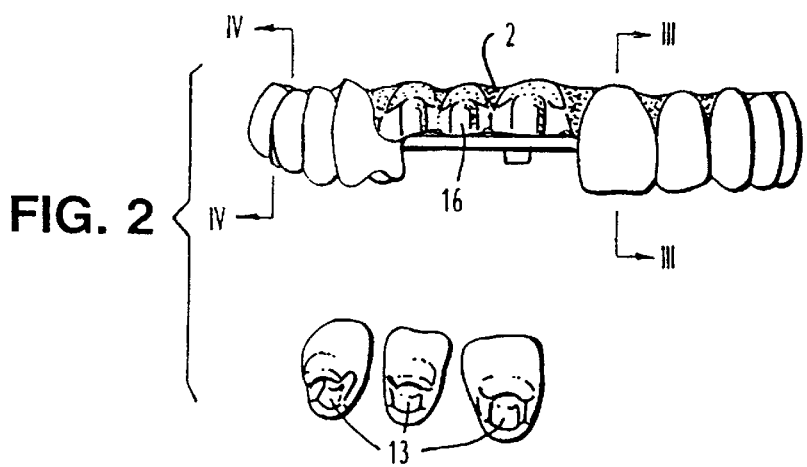
FIG. 2

DEVICE FOR DISPENSING ARTIFICIAL TEETH

FIELD OF THE INVENTION

The invention relates to a device on which artificial teeth are arranged, and to a method of dispensing artificial teeth in the formation of a set of dentures.

BACKGROUND OF THE INVENTION

The use of artificial teeth and dentures to replace natural teeth has been known for centuries. In modern times, artificial teeth are made chiefly from polymethyl methacrylate and to a lesser extent from the glass-ceramics and from dental porcelains. To prepare a complete artificial denture for a patient, the dentist first takes impressions of the patient's residual dental arches, from which the natural teeth have been lost. An impression material like polysiloxane can be used. An impression is taken of the patient's upper jaw and a lower impression of the lower jaw. Artificial dental stone casts or models are poured from these impressions. On these casts, wax rims are prepared and these rims are carved by the dentist until the correct facial and lip contours are supported by them. The rims are finally fixed together in occlusion i.e. in contact, to register the relationship of the lower jaw to the upper jaw, commonly known as "the bite". Artificial teeth are set-up into the wax occlusion rims to trial denture stage by the dentist, or more usually by a dental technician. Wax-based trial dentures, with the artificial teeth affixed, are then assessed for appearance and fit in the patient's mouth. When an acceptable appearance, good fit and correct bite are achieved, the wax of the trial dentures is replaced with acrylic. This is done by making a gypsum mould for each denture, upper and lower, and by boiling out the wax. It is replaced with a material like polymethyl methacrylate. The teeth on the plastics dentures are in the same position as they were in the wax trial dentures.

Conventionally, artificial teeth are supplied by a manufacturer arranged on four separate tooth-cards. Typically, there are the six upper anterior teeth, the six lower anterior teeth, the eight upper posterior teeth (four on either side) and the eight lower posterior teeth (four on either side). The teeth are matched by mould and by shade and the manufacturer can dispense the four cards as a display unit. A dentist may use the teeth as a set, for a complete artificial dentition, but the customary method of arranging the teeth of artificial dentures is to remove individual teeth from the cards and place them on the wax bases until they simulate the natural teeth of a patient. Eventually, fourteen upper teeth are set-up on a wax base and fourteen lower teeth on a lower wax rim are prepared as a complete trial denture of up to twenty-eight teeth. The positions of the teeth can be further adapted by the dentist to the exact requirements of a patient before the dentures are completed.

DE-A-39 10 393 relates to an external jig having an arch-shaped hollow frame (1) in which is formed a plurality of shaped apertures (8) to receive the occlusal surfaces (i.e. cut ring surfaces) of artificial teeth. Thus, the "backs" or bases of the teeth extend outwardly of the jig so that they can be pressed by the jig into the underlying wax baseplate (5).

The known arrangements have the disadvantage that they are very time consuming. Because each tooth must be set individually on a wax trial base or on a jig, it can take a dental technician several hours to set the teeth correctly. Also, considerable skill is required in selecting the particular teeth to achieve dentures having a desired cosmetic effect and with a harmonious occlusion between upper and lower sets of teeth.

OBJECTION OF THE INVENTION

It is an object of the invention to overcome the aforesaid disadvantage and to provide a device and method by means of which the teeth can be dispensed by the manufacturer in a pre-arranged ideal anatomical and geometrical arrangement which simplifies the task of a dental technician or dentist in forming a set of artificial dentures.

SUMMARY OF THE INVENTION

A device for dispensing artificial teeth comprising an arch-shaped support including means for removably mounting a set of artificial teeth on the arch characterised in that the device comprises a tooth support ribbon made from a flexible material and shaped to form an arch which substantially corresponds in shape to an upper or lower natural dental arch, mounting means by means of which the backs of the teeth are affixed to the ribbon, and means to vary the radius of the ribbon arch, the teeth being arranged on the ribbon in an order which simulates natural dentition, whereby the ribbon may be set-up into trial occlusion rims (blocks) of wax or the like in the production of dentures.

Preferably, the means comprises an extensible cross-member connected at each end to the ribbon and extending across the arch. The cross-member may be adjusted in length to expand or contract the radius of the arch.

The means for attaching the teeth to the ribbon preferably comprises a slot in each tooth which engages with keys formed in the ribbon. Suitably, the ribbon is moulded with a plurality of sockets shaped to receive the keys in the backs of the teeth. The size of the slot and of the key will vary for each tooth in the set. Every slot or key is individual for one particular tooth. Thus, a tooth cannot be placed on the arch incorrectly. Thus, dentists and technicians cannot mix-up the teeth. It is possible to use, for example, an upper right lateral tooth from another ribbon, but the key in the ribbon will not accept an upper left lateral by mistake.

In addition to the fixing means, a thin film of tooth-carding wax may be used to assist in retaining the teeth on the ribbon.

Preferably, the device comprises two ribbon arches, one having a set of teeth for the upper jaw and the other accepting a set of teeth for the lower jaw, the teeth of the upper arch contacting the teeth of the lower arch in occlusal harmony, as manufactured.

The invention includes a method of dispensing artificial teeth in the formation of a set of artificial dentures which comprises the steps of:

a) taking a device as described above containing a set of artificial teeth pre-arranged on the ribbon in a pre-arranged ideal anatomical and geometrical arrangement, b) placing one ribbon arch, preferably the upper teeth arch, on the surface of a wax occlusion block, c) adjusting the radius of the ribbon arch to correspond to the clinical requirement of the patient, and d) adjusting the radius of a second ribbon arch, preferably the lower teeth arch, such that it occludes accurately with the upper arch.

BRIEF DESCRIPTION OF THE DRAWINGS

Some embodiments of the invention are hereinafter described with reference to the accompanying drawings, wherein:

FIG. 1 is a plan view of an upper ribbon arch of the invention prior to the attachment of teeth;

FIG. 2 is an elevation view, similar to FIG. 1, showing some teeth attached to the ribbon;

FIG. 3 is a sectional elevation through the upper left incisor tooth on the line III—III of FIG. 2;

FIG. 4 is a sectional elevation through the upper right first molar tooth on the line IV—IV of FIG. 2;

DESCRIPTION OF THE PREFERRED EMBODIMENT

Figure 5:
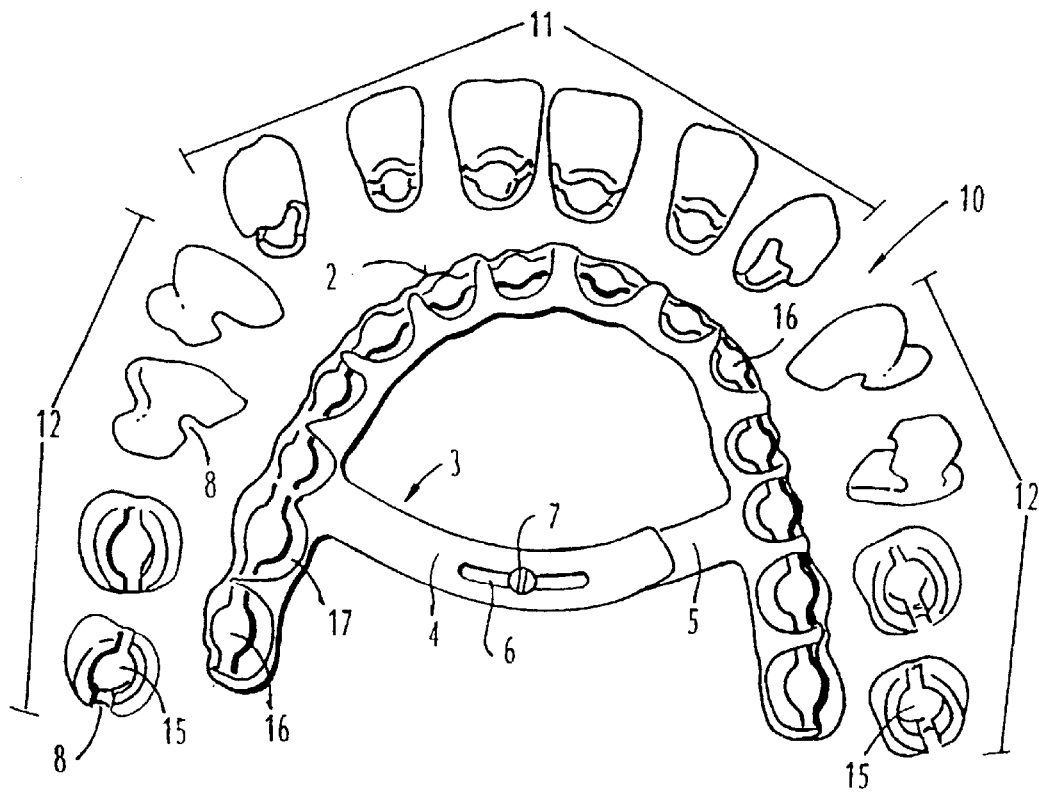
FIG. 5 is a plan view of a second embodiment of a ribbon arch with a set of artificial teeth disposed alongside prior to attachment to the ribbon.
Figure 6:
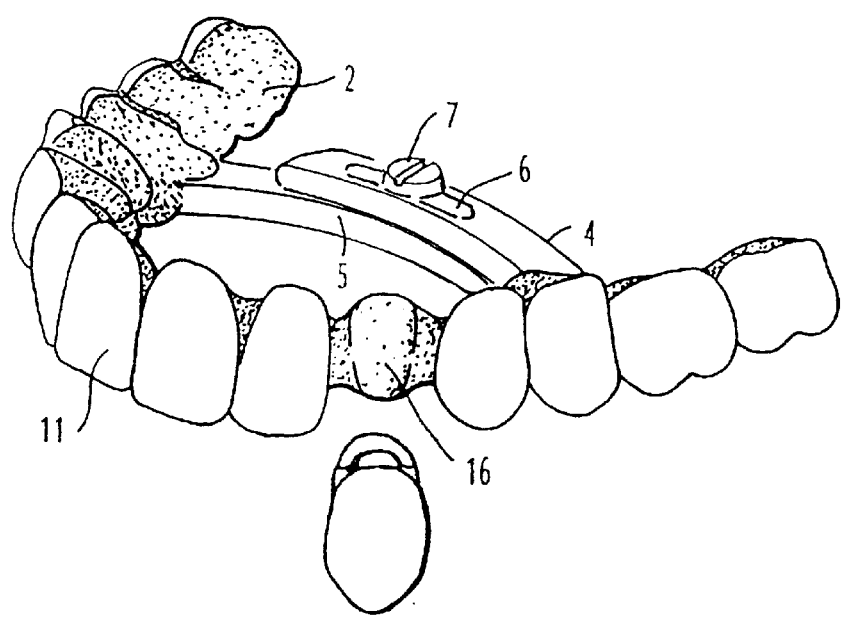
FIG. 6 is a perspective view of the ribbon of FIG. 5 with the teeth attached.

The first embodiment of a device for dispensing artificial teeth in accordance with the invention is shown in FIGS. 1 to 6 of the accompanying drawings. It is of the upper set of teeth. The device 1 comprises a ribbon 2 in the shape of an arch. Suitably, the ribbon 2 is made from a plastics material. Polypropylene has been found suitable. Polymethyl methacrylate, polycarbonate or any suitable plastic material either filled or unfilled, or thermally sensitive or not, to give the appropriate flexibility/rigidity can be used. Metal wire e.g. stainless steel can be used also. A metal wire is preferably of square cross-section. It can be run through the diatoric holes in the teeth or it can be fixed to the backs of the teeth with polymethyl methacrylate. The ribbon 2 may be made by injection moulding procedures although other means such as, vacuum-forming can be employed. Preferably, the ribbon 2 is coloured pink to simulate the gums.

An extensible cross-member 3 extends across the arch. The cross-member 3 is made up of overlapping sections 4, 5. The sections 4, 5 are connected at their inner ends to the ribbon 1 at an intermediate location on the arch, and overlap each other in sliding arrangement. A bolt 7 engages in a slot 6 formed on the overlapping portions of the sections 4, 5. Thus, the length of the cross-member 3 can be adjusted by sliding the sections 4, 5 relative to each other, and then locking them in position by means of the bolt 7.

The extensible cross-member 3 serves a number of functions. Firstly, it helps to maintain the ribbon 1 in an arch-shape. It strengthens the arch and also allows expansion or contraction of the radius of the arch to conform with the shape of the patient's jaw. Suitably, the cross-member 3 is made from the same plastics material as the ribbon 2 and is preferably moulded integrally with the ribbon 2.

The invention includes means for mechanically attaching a set 10 of artificial teeth to the support ribbon 2. The set of teeth 10 suitably comprises from twelve to sixteen teeth, but preferably comprises fourteen teeth, made up of six anterior teeth 11 and eight posterior teeth 12 (see FIG. 5).

Artificial veneers may be substituted for artificial teeth where appropriate. The teeth 11, 12 or veneers are preferably made of polymethyl methacrylate, but porcelain or glass-ceramic can be used along with an appropriate silane coupling agent to the denture base e.g.-methacryloxy propyltrimethoxy silane. This is a chemical bonding agent which is applied to glass-ceramic or porcelain teeth before the acrylic base of the denture is cured or processed onto the teeth.

As shown more particularly in FIGS. 1 and 5, the teeth 11, 12 are formed with internal slots 13 formed in the backs 14 of the teeth. Suitably the slots 13 are of cruciform shape having a main part 15 which extends through the tooth, but also includes two laterally extending portions 8 which open into the side surfaces of the tooth, known dentally as the mesial and distal surfaces of teeth.

The slots 13 engage with complementary cruciform-shaped keys 16 moulded in the surface of the ribbon 2. The keys 16 also define sockets 17 which receive the "backs" or bases of the artificial teeth.

Alternatively, the slots 13 are in the form of round holes which receive a pop-stud type key moulded in the surface of the ribbon 2.

The teeth are held firmly in place on the ribbon 2 by means of the slot and key arrangement. However, each individual tooth 11, 12 may be readily removed from the ribbon 2 as required. To assist in affixing the teeth 11, 12 to the ribbon 2, a thin film of carding wax may be applied to the keys 16. Thus, the teeth are secured on the arches temporarily by a layer of carding wax or equivalent material.

The slots 13 in the teeth add to the bonding of the teeth to the base plastics of the finished denture, to prevent peeling-off of the teeth from the denture base.

In use, the teeth 11, 12 can be removed and replaced on the ribbon arch 2 at will, to simulate the arrangement required by the patient. When using the dental arch of the invention, the dentist or dental technician takes the ribbon arch as supplied by the manufacturer containing a set 10 of artificial teeth applied in a pre-arranged ideal anatomical and geometrical arrangement. Thus, typically, the set will contain 14 teeth arranged to simulate the natural dentition. The ribbon of upper teeth is placed onto the surface of the upper wax occlusion block which was decided by the dentist to be the correct lip and cheek contours of the patient. The level of the incisor teeth and the level of the cusps of the posterior teeth are set to the level shown by that on the wax rim. Ideally a patient shows 2 mm of incisor tooth with the lip at rest, and the whole length of the upper front teeth when smiling. The ribbon of lower teeth is then set at the correct radius to occlude accurately with the upper arch of teeth, and the lower arch is fixed to the upper teeth temporarily with wax. If the occlusion rim has been adjusted correctly by the dentist only minor adjustment of the alignment of the posterior teeth should be necessary to bring the teeth over the lower jaw. Both upper and lower trial dentures can be waxed-up around the teeth.

In general the ribbon arch of the invention would be used chiefly by dental technicians, but can also be employed by the dentist during the clinical stages, and without intervention of a technician. The ribbon 2 can be divided and used in sextents, for example the upper set of anteriors 11 in a partial denture.

By adjusting the cross-member 3, the arch form is capable of expansion and contraction to meet the clinical requirements of the patient. The ribbon 2 can be cut easily to remove its intrinsic flexible memory, after arranging the teeth. That is to neutralize their resiliency (by bending), after setting-up and after removal of the cross-member 3. Also, the ribbon 2 is capable of being removed locally (after setting-up) so that an individual tooth can be arranged differently from that of the original. The cross-member is left in position on the trial dentures to prevent distortion of the wax bases. It is best removed by the dentist, because the upper cross-member can be tried in the mouth. The teeth can be waxed-up to simulate the "norm" or any appropriate gingival characteristic, or to reduce the apparent size of a tooth or series of teeth e.g. in a young person only the crowns of the teeth would be visible. Whereas, in an elderly person the crowns and parts of the roots of the teeth might be exposed.

The ribbon arch of the invention containing a set of teeth can be set-up on a simple articulator, and still obtain excellent articulation and balance of the occulsion.

In most cases, the ribbon arch 2 is removed at the boil-out stage of flasking and is not incorporated into the final denture. However, where the ribbon is made from metal (e.g. stainless steel) wire, the wire could be incorporated into the final denture and will add a radiopaque tracer to the denture. Normal acrylic dentures do not show on a radiograph.

The ribbon arches 2 are intended to be discarded after use, but are standard for most sizes of teeth and could be reused. For example, teeth left over from partly used sets could be carded onto another ribbon arch to make a unit. Anterior teeth of different sets can be mixed to simulate individuality.

Figure 7:
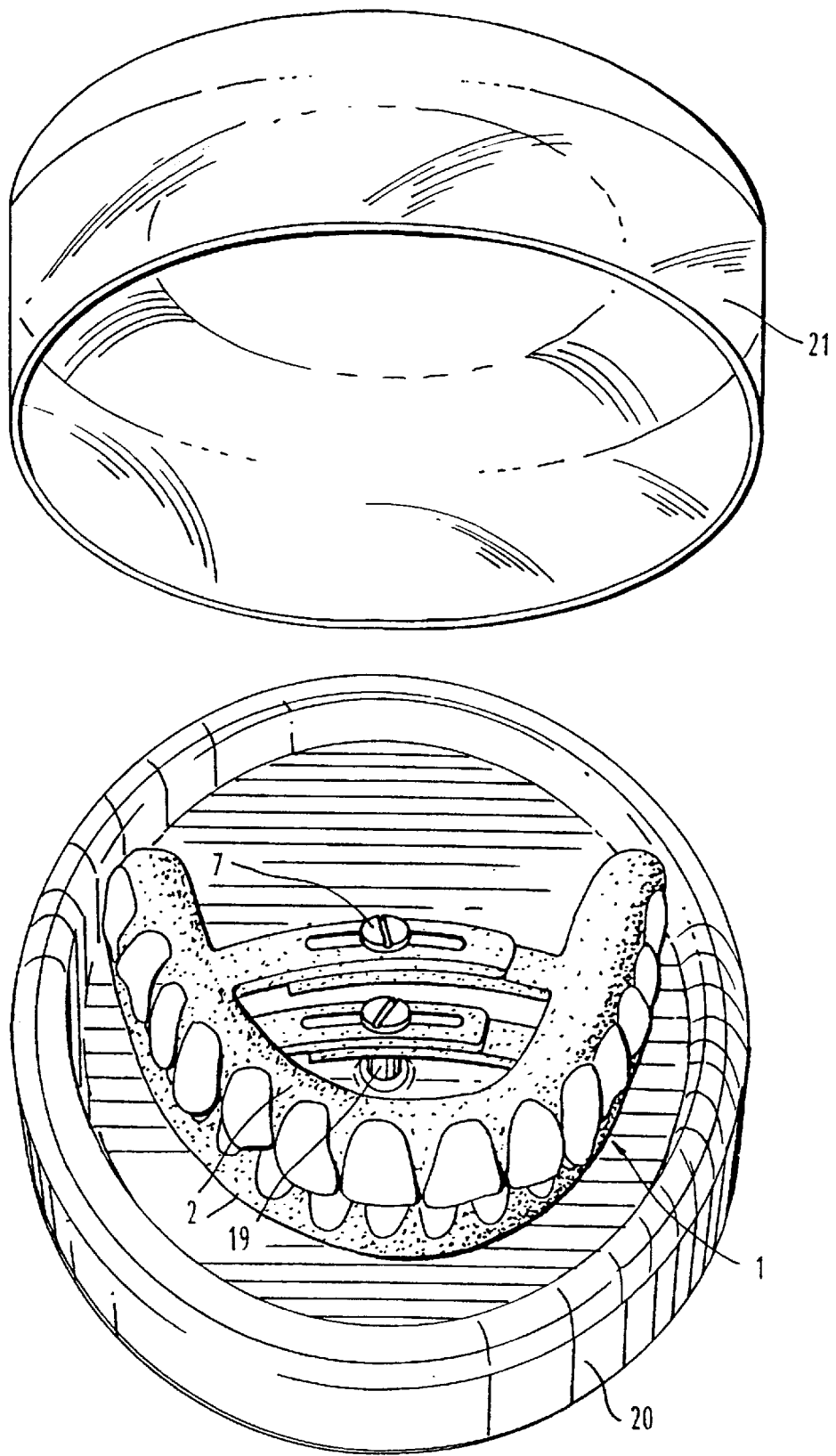
FIG. 7 shows a container and lid for presentation of a set of upper and a set of lower teeth on devices of the invention.

FIG. 7 illustrates a method of packaging the device of the invention. This shows two devices 1 of the invention, comprising an upper ribbon 2 containing a set of teeth for the upper jaw, and a lower ribbon 2 containing a set of teeth for the lower jaw. The two sets are shown occluded and are held together by means of the bolt 7 which extends through the cross-members 3 of each set, supported by a pillar 19 mounted on a support tray 20. The support tray is provided with a cover 21 which, preferably, is comprised partly of a transparent material, so that the teeth are visible through the cover.

The device of the invention offers a number of advantages over conventional methods of dispensing artificial teeth. Firstly, the artificial teeth are already arranged to the ideal situation, which can be modified easily to the particular. Less expertise is required of the dentist and technician. Less time is required to complete the arrangement of the teeth, for example, the teeth can be set up in minutes as opposed to hours with the conventional method. Thus, the device of the invention provides a very cost-effective method. The conventional method of setting up teeth can still be used with the suggested tooth cards of the invention.

What is claimed is:

1. A device for arranging and dispensing artificial teeth including an arch-shaped support and means for removably mounting a set of artificial teeth on the arch-shaped support wherein the device comprises a tooth support ribbon made from a flexible material and shaped to form an arch which substantially corresponds in shape to an upper or lower natural dental arch, mounting means for removably affixing the backs of the teeth to the ribbon and means for varying the radius of the ribbon arch, the teeth being arranged on the ribbon in an order which simulates natural dentition.

2. A device as claimed in claim 1, wherein the means for varying the radius of the arch comprises an extensible cross-member connected to the tooth support ribbon and extending across the arch, such that adjustment of cross-member length expands or contracts the radius of the arch.

3. A device as claimed in claim 2, wherein the extensible cross-member comprises two overlapping sections, one section being connected to the ribbon at one side of the arch, and the other section being connected to the ribbon at the opposite side of the arch, and the sections overlap each other in sliding arrangement, and locking means for locking the sections in a desired position.

4. A device as claimed in claim 1, wherein the means for removably affixing the teeth to the ribbon comprises a slot in each tooth which engages with a complementary key formed in the ribbon.

5. A device as claimed in claim 4, wherein the slots are substantially of cruciform shape and engage with the keys which are of complementary cruciform shape.

6. A device as claimed in claim 5, wherein the size of each slot and the complementary key varies for each tooth of the set of teeth such that every slot and its associated key is individual for one particular tooth.

7. A device as claimed in claim 1, further comprising two ribbon arches, one having a set of teeth for the upper jaw and the other having a set of teeth for the lower jaw, the teeth of the upper arch being arranged to contact the teeth of the lower arch in occlusal harmony.

8. A device as claimed in claim 1, wherein the teeth are temporarily secured on the ribbon by securing means.

9. A device as claimed in claim 8, wherein the securing means is carding wax.

10. For a device for arranging and dispensing artificial teeth, the device including two ribbon arches, one having a set of teeth for the upper jaw and the other having a set of teeth for the lower jaw, a method of arranging artificial teeth in the formation of a set of artificial dentures which comprises the steps of:

a) providing a set of artificial teeth pre-arranged on the ribbons in a pre-arranged ideal anatomical and geometrical arrangement, b) placing a first ribbon arch on the surface of a wax occlusion block, c) adjusting the radius of the first ribbon arch to correspond to the clinical requirement of the patient, and d) adjusting the radius of a second ribbon arch such that it occludes accurately with the upper arch.

* * * * *